US012336924B2

(12) United States Patent
Ross

(10) Patent No.: US 12,336,924 B2
(45) Date of Patent: Jun. 24, 2025

(54) JOINT REHABILITATING GARMENT ASSEMBLY

(71) Applicant: Shavin Ross, Sunnyvale, CA (US)

(72) Inventor: Shavin Ross, Sunnyvale, CA (US)

( * ) Notice: Subject to any disclaimer, the term of this patent is extended or adjusted under 35 U.S.C. 154(b) by 547 days.

(21) Appl. No.: 17/714,699

(22) Filed: Apr. 6, 2022

(65) Prior Publication Data
US 2023/0320883 A1    Oct. 12, 2023

(51) Int. Cl.
| | | |
|---|---|---|
| *A61F 5/01* | (2006.01) | |
| *A41B 1/00* | (2006.01) | |
| *A41F 15/00* | (2006.01) | |
| *A61F 5/02* | (2006.01) | |
| *A63B 21/00* | (2006.01) | |
| *A63B 21/055* | (2006.01) | |

(52) U.S. Cl.
CPC .............. *A61F 5/0118* (2013.01); *A41B 1/00* (2013.01); *A61F 5/013* (2013.01); *A41F 15/00* (2013.01); *A61F 2005/0197* (2013.01); *A61F 5/026* (2013.01); *A63B 21/0552* (2013.01); *A63B 21/4025* (2015.10)

(58) Field of Classification Search
CPC ............ A61F 5/0118; A61F 2005/0197; A61F 5/013; A61F 5/02; A61F 5/026; A61F 5/05808; A61F 5/05858; A61F 5/37; A61F 5/3715; A61F 5/3723; A41D 13/0002; A41D 13/0005; A41D 13/0007; A41D 13/0015; A41D 2300/22; A41F 3/00; A41F 3/02; A41F 3/04; A41F 3/045; A41F 3/06; A41F 5/00; A41F 15/00; A41F 15/002; A41F 15/005; A41F 15/007; A61H 1/00; A61H 1/02; A61H 1/0274; A61H 1/0281; A63B 21/00; A63B 21/02; A63B 21/055; A63B 21/0552; A63B 21/4025; A41B 1/08
USPC ..................... 2/117, 122, 461; 482/121, 124
See application file for complete search history.

(56) References Cited

U.S. PATENT DOCUMENTS

| | | | | | |
|---|---|---|---|---|---|
| 2,526,785 A | * | 10/1950 | Werber | ...................... | A41F 5/00 2/117 |
| 2,682,669 A | * | 7/1954 | Valentine | .................. | A41F 3/00 2/310 |
| 3,027,898 A | * | 4/1962 | Williams | ................ | A41F 15/00 450/86 |
| 5,072,457 A | * | 12/1991 | Aronne | .............. | A41D 13/0007 2/102 |

(Continued)

*Primary Examiner* — Keri J Nelson
*Assistant Examiner* — Seth R. Brown

(57) ABSTRACT

A joint rehabilitating garment assembly includes a shirt that is wearable on a user's torso such that the shirt covers each of the user's shoulders. The shirt has a plurality of channels integrated into the shirt and each of the channels is strategically positioned on the shirt such that each of the channels extends along pre-determined pressure points associated with supporting a rotator cuff injury in the user. A plurality of elastomeric bands is each of the elastomeric bands is routed through respective ones of the channels in the shirt thereby facilitating each of the elastomeric bands to extend along the pre-determined pressure points associated with rotator cuff injuries. Each of the elastomeric bands imparts tension into the pre-determined pressure points to support the user's rotator cuffs while the user's rotator cuffs are healing from injury.

12 Claims, 5 Drawing Sheets

(56) References Cited

U.S. PATENT DOCUMENTS

| | | | | |
|---|---|---|---|---|
| 5,691,028 A * | 11/1997 | Curtis | | A41F 15/007 428/36.1 |
| 5,745,917 A | 5/1998 | Dicker | | |
| 5,820,534 A * | 10/1998 | Vadher | | A63B 21/4005 482/125 |
| 6,125,475 A * | 10/2000 | Taylor | | A41F 3/00 2/326 |
| 7,608,026 B1 * | 10/2009 | Nicassio | | A63B 21/4015 482/121 |
| 7,891,023 B1 * | 2/2011 | Hill | | A41F 3/00 2/310 |
| D751,276 S | 3/2016 | Puni | | |
| 10,143,878 B2 | 12/2018 | Gottfried | | |
| 11,839,243 B1 * | 12/2023 | Solotoff | | A41D 13/0531 |
| 2009/0126084 A1 * | 5/2009 | Fenske | | A61F 5/026 2/243.1 |
| 2010/0077527 A1 | 4/2010 | Lee | | |
| 2010/0093504 A1 * | 4/2010 | Del Monte | | A63B 21/065 473/446 |
| 2011/0197335 A1 * | 8/2011 | Handy | | A41F 5/00 2/117 |
| 2013/0067628 A1 * | 3/2013 | Harb | | A63B 21/00061 2/69 |
| 2013/0326785 A1 | 12/2013 | Cornacchiari | | |
| 2014/0325732 A1 | 11/2014 | Anderson | | |
| 2015/0067951 A1 * | 3/2015 | Johnsen | | A63B 33/004 2/431 |
| 2015/0272769 A1 * | 10/2015 | Pelaez | | A61F 5/02 602/18 |
| 2018/0133047 A1 * | 5/2018 | Nakamitsu | | A61F 5/3753 |
| 2019/0343670 A1 * | 11/2019 | Ruprecht | | A61H 1/0274 |
| 2020/0069990 A1 * | 3/2020 | Smith-Miles | | A41D 1/04 |
| 2020/0288798 A1 * | 9/2020 | Atallah | | A41D 31/245 |
| 2021/0128338 A1 | 5/2021 | Ava | | |
| 2022/0219312 A1 * | 7/2022 | Schirrmeister | | A61F 5/013 |
| 2023/0292855 A1 * | 9/2023 | Shaffer | | A41D 13/0512 2/461 |

\* cited by examiner

US 12,336,924 B2

JOINT REHABILITATING GARMENT ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to joint rehabilitating devices and more particularly pertains to a new joint rehabilitating device for supporting an injured shoulder joint during the rehabilitation process. The device includes a shirt and a plurality of channels integrated into the shirt strategically aligned with a user's shoulders. The device includes a plurality of elastomeric bands that each extends through respective channels. In this way the elastomeric bands impart tension into the user's shoulders to support the user's shoulders to rehabilitate the user's shoulder after injury or reconstructive surgery.

(2) Description of Related Art Including Information Disclosed Under 37 CFR 1.97 and 1.98

The prior art relates to joint rehabilitating devices including a variety of body garment devices that includes elastomeric resistance bands extending along arms, legs and a torso of the body garment to assist with aerobic exercise. The prior art discloses a shirt which has elastomeric bands extending through each of the sleeves of the shirt and which includes thumb loops integrated into the elastomeric bands for positioning around the user's thumbs. The prior art discloses a variety of shirts that each includes elastomeric elements each integrated into respective sleeves of the shirt for facilitating neuro-musculo-skeletal assistance. The prior art discloses an ornamental design for a shoulder stabilizing shirt that includes elastomeric bands arranged in a cross-cross pattern in a shirt.

BRIEF SUMMARY OF THE INVENTION

An embodiment of the disclosure meets the needs presented above by generally comprising a shirt that is wearable on a user's torso such that the shirt covers each of the user's shoulders. The shirt has a plurality of channels integrated into the shirt and each of the channels is strategically positioned on the shirt such that each of the channels extends along pre-determined pressure points associated with supporting a rotator cuff injury in the user. A plurality of elastomeric bands is each of the elastomeric bands is routed through respective ones of the channels in the shirt thereby facilitating each of the elastomeric bands to extend along the pre-determined pressure points associated with rotator cuff injuries. Each of the elastomeric bands imparts tension into the pre-determined pressure points to support the user's rotator cuffs while the user's rotator cuffs are healing from injury.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
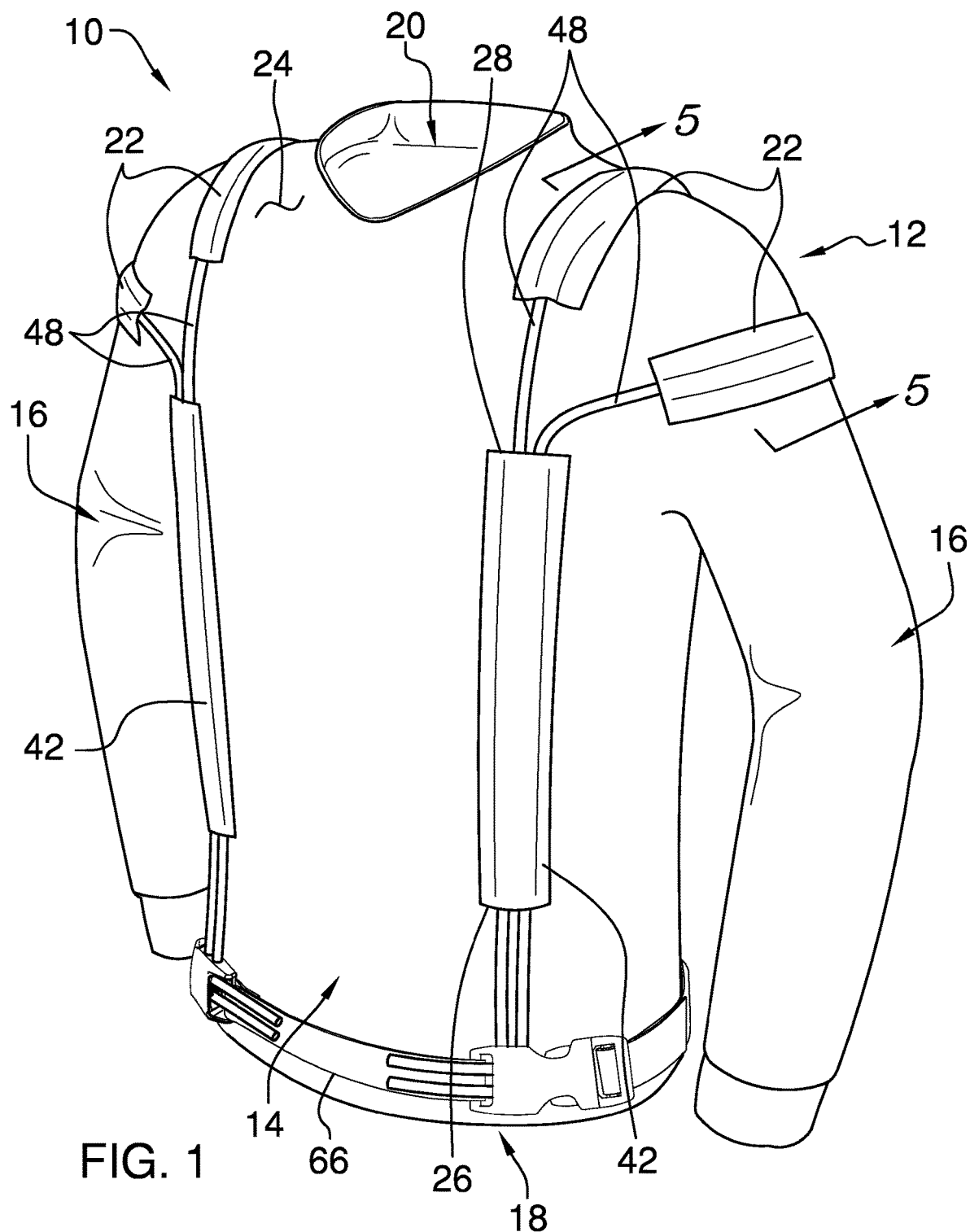
FIG. 1 is a front perspective view of a joint rehabilitating garment assembly according to an embodiment of the disclosure.
Figure 2:
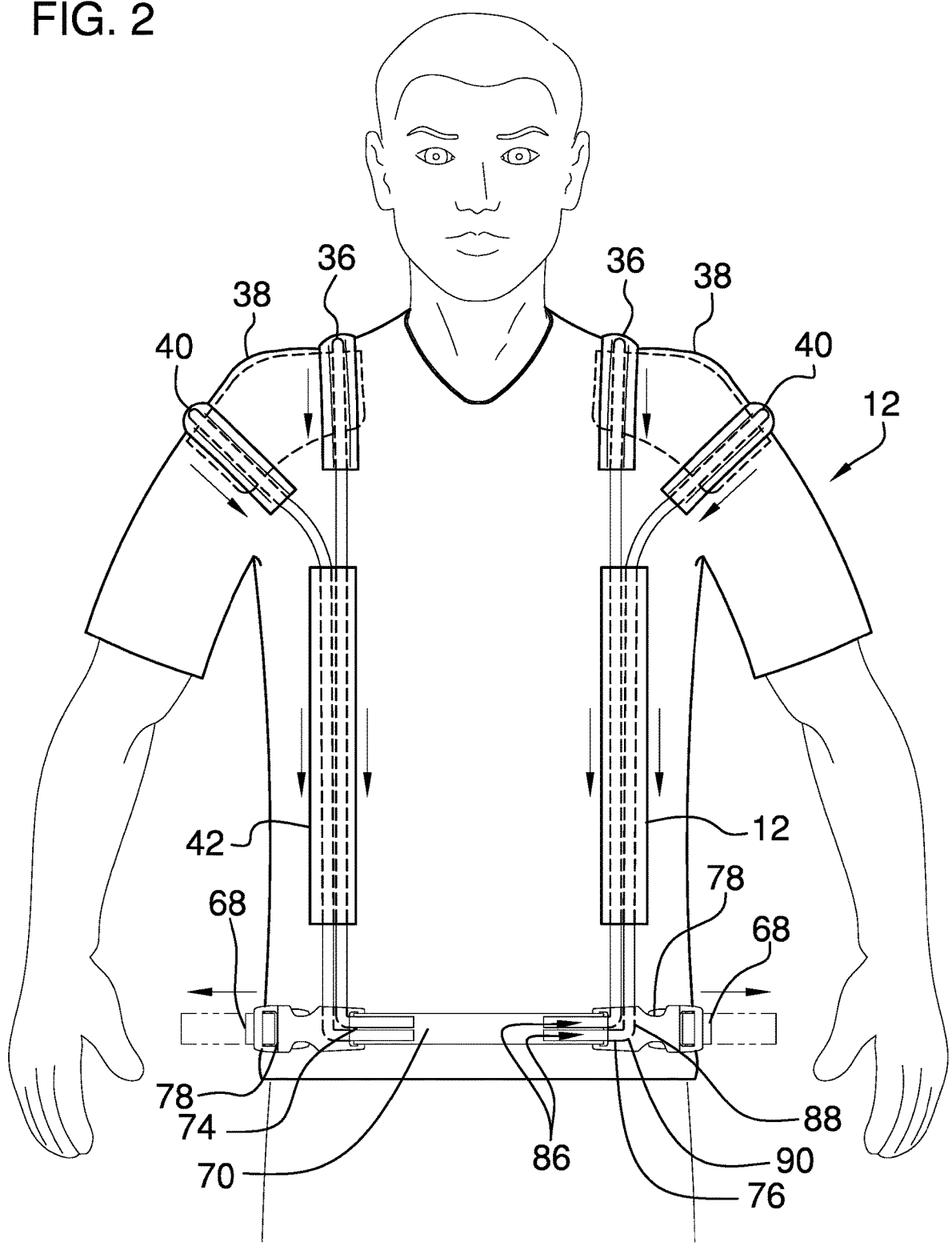
FIG. 2 is a front in-use view of an embodiment of the disclosure.
Figure 3:
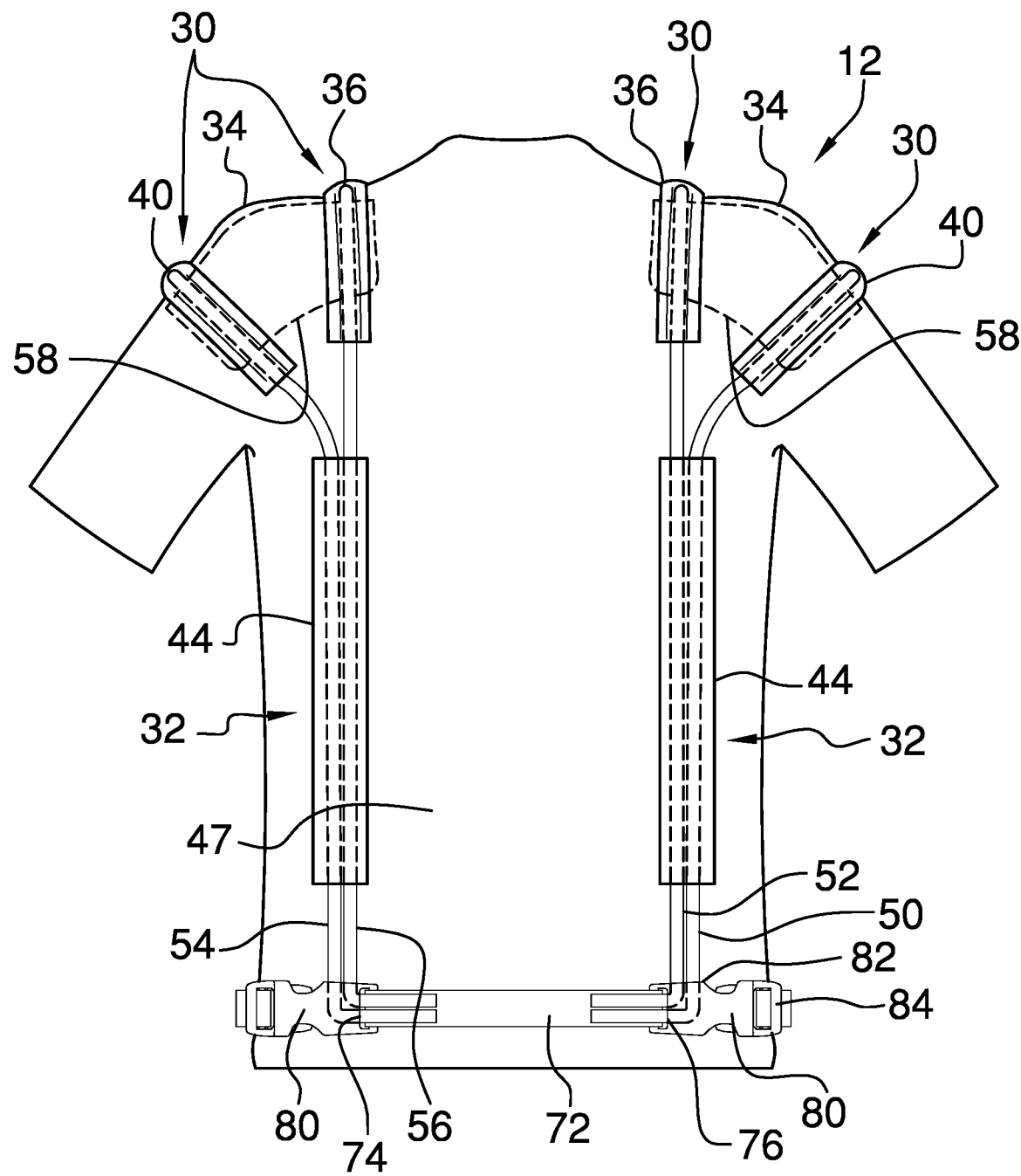
FIG. 3 is a back phantom view of an embodiment of the disclosure.
Figure 4:
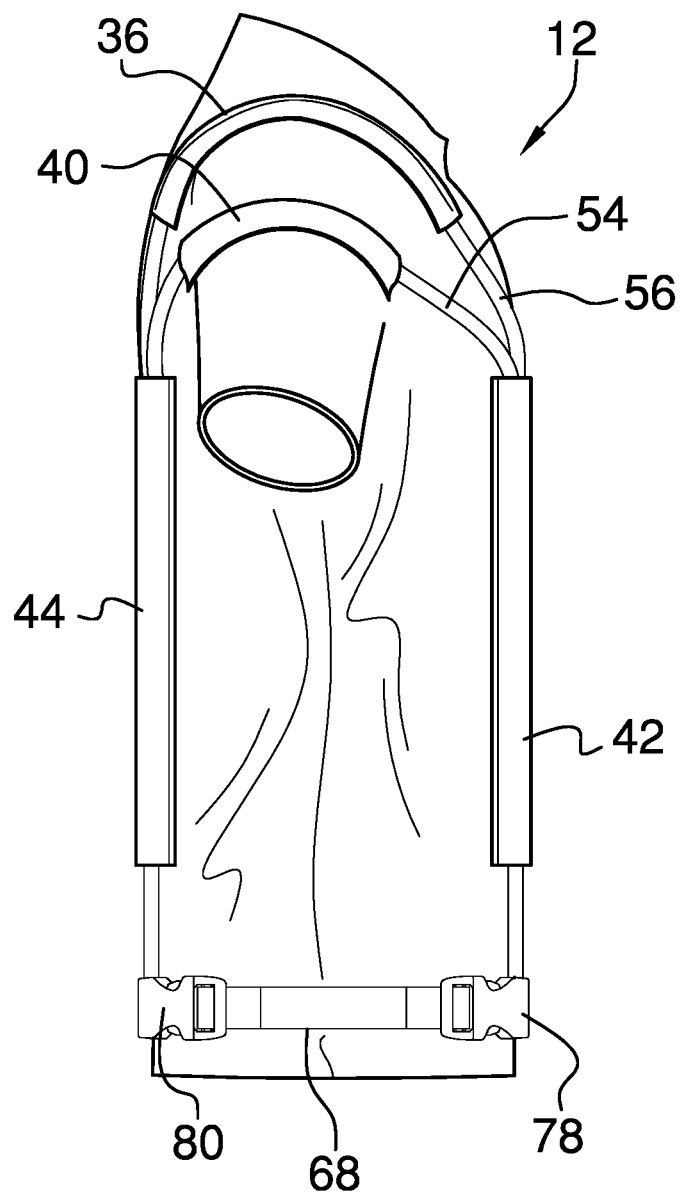
FIG. 4 is a right side view of an embodiment of the disclosure.
Figure 5:
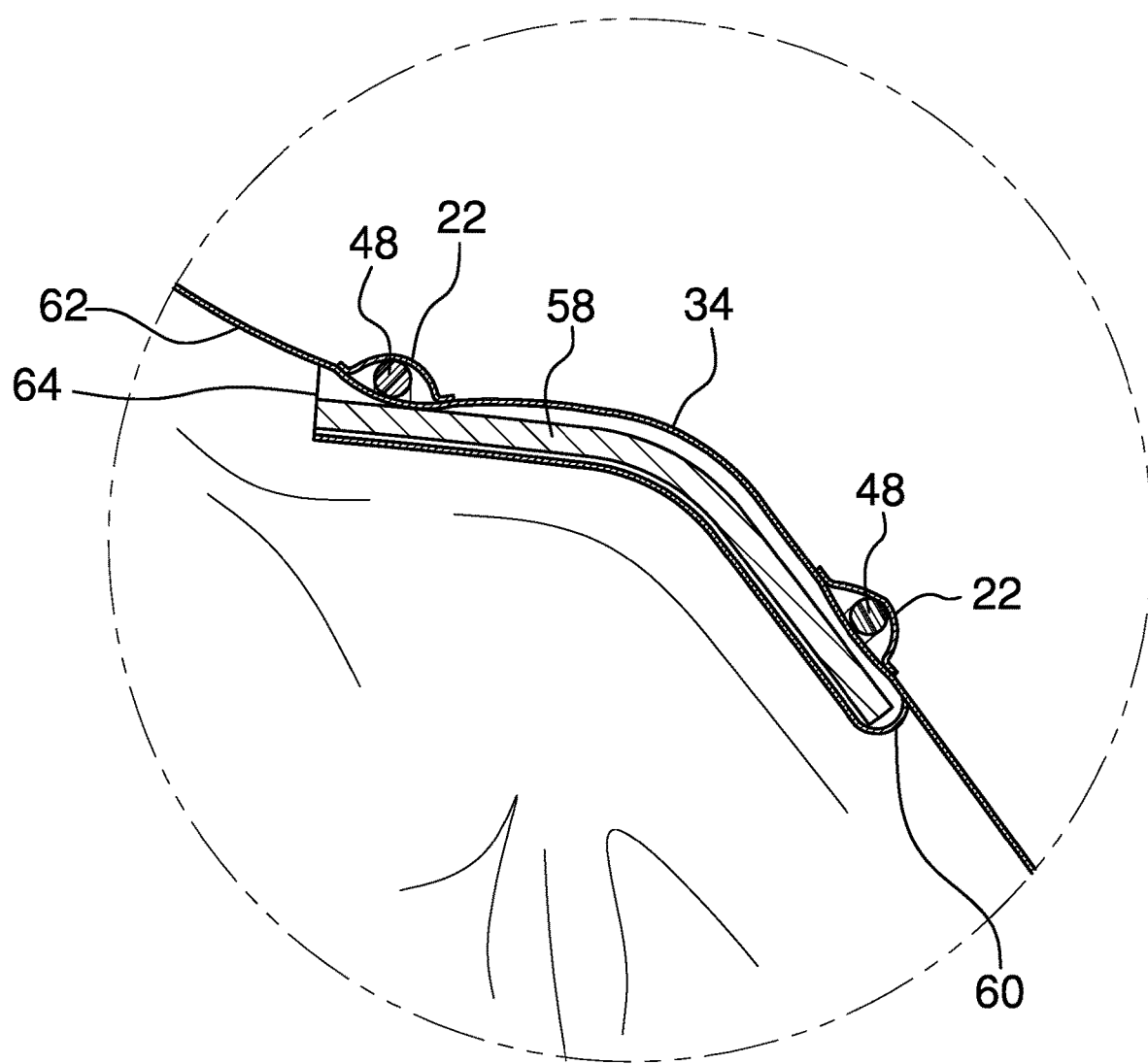
FIG. 5 is a cross sectional view taken along line 5-5 of FIG. 1 of an embodiment of the disclosure.

With reference now to the drawings, and in particular to FIGS. 1 through 5 thereof, a new joint rehabilitating device embodying the principles and concepts of an embodiment of the disclosure and generally designated by the reference numeral 10 will be described.

As best illustrated in FIGS. 1 through 5, the joint rehabilitating garment assembly 10 generally comprises a shirt 12 that is wearable on a user's torso such that the shirt 12 covers each of the user's shoulders, and the shirt 12 has a body portion 14, a pair of sleeves 16, a waist 18 and a neck 20. Furthermore, the shirt 12 may be a long sleeved shirt or a short sleeved shirt and the shirt 12 may be styled in any manner that is common to either short sleeved shirts or long sleeved shirts. The shirt 12 has a plurality of channels 22 integrated into the shirt 12 and each of the channels 22 is strategically positioned on the shirt 12 such that each of the channels 22 extends along pre-determined pressure points associated with supporting a rotator cuff injury in the user.

Each of the channels 22 is integrated into an outer surface 24 of the shirt 12 and each of the channels 22 has a first end 26 and a second end 28. Additionally, each of the first end 26 and the second end 28 of each of the channels 22 is open and each of the channels 22 is hollow. The plurality of channels 22 includes a pair of sets of shoulder channels 30 and a pair of sets of torso channels 32. Each of the sets of shoulder channels extends over a respective shoulder 34 of the shirt 12 such that each of the shoulder channels 22 extends over a respective one of the user's shoulders when the shirt 12 is worn.

Each of the sets of shoulder channels 30 includes a first shoulder channel 36 that is positioned between the neck 20 and a crown 38 of a respective one of the shoulders 34 of the shirt 12. In this way the first shoulder channel 36 of each of the set of shoulder channels 22 extends over a respective one of the user's supraspinatus tendon. Each of the sets of shoulder channels 30 includes a second shoulder channel 40 that is positioned on an opposing side of the crown 38 of the respective shoulder 34 of the shirt 12 with respect to a respective one of the first shoulder channels 36. In this way wherein the second shoulder channel 40 of each of the sets of shoulder channels 30 extends over a respective one of the user's deltoid muscles.

Each of the sets of torso channels 32 is vertically oriented to extend along an axis extending between the neck 20 and the waist 18 of the shirt 12, and each of the sets of torso channels 32 includes a first torso channel 42 and a second torso channel 44. The first torso channel 42 of each of the sets of torso channels 32 is positioned on a front side 46 of the body portion 14 of the shirt 12 and the first torso channel 42 of each of the sets of torso channels 32 is positioned on opposing sides of a center line of the body portion 14 with respect to each other. The second torso channel 44 of each of the sets of torso channels 32 is positioned on a back side 47 of the body portion 14 of the shirt 12 with respect to each other and the second torso channel 44 of each of the sets of torso channels 32 is positioned on the front side 46 of the body portion 14 of the shirt 12. Furthermore, the second torso channel 44 of each of the sets of torso channels 32 is positioned on opposing sides of the center line of the body portion 14 of the shirt 12.

A plurality of elastomeric bands 48 is each routed through respective ones of the channels 22 in the shirt 12 thereby facilitating each of the elastomeric bands 48 to extend along the pre-determined pressure points associated with rotator cuff injuries. Each of the elastomeric bands 48 imparts tension into the pre-determined pressure points to support the user's rotator cuffs while the user's rotator cuffs are healing from injury. The plurality of elastomeric bands 48 includes a first band 50, a second band 52, a third band 54 and a fourth band 56. The first band 50 extends through the first torso channel 42 of a respective one of the sets of torso channels 32 and the second shoulder channel 40 of a respective one of the sets of shoulder channels 30 and the second torso channel 44 of a respective one of the sets of torso channels 32. The second band 52 extends through the first torso channel 42 of a respective one of the sets of torso channels 32 and the first shoulder channel 36 of a respective one of the sets of shoulder channels 30 and the second torso channel 44 of a respective one of the sets of torso channels 32. The third band 54 extends through the first torso channel 42 of a respective one of the sets of torso channels 32 and the second shoulder channel 40 of a respective one of the sets of shoulder channels 30 and the second torso channel 44 of a respective one of the sets of torso channels 32. The fourth band 56 extends through the first torso channel 42 of a respective one of the sets of torso channels 32 and the first shoulder channel 36 of a respective one of the sets of shoulder channels 30 and the second torso channel 44 of a respective one of the sets of torso channels 32. Additionally, each of the first band 50 and the second band 52 extends through the same first torso channel 42 and the same second torso channel 44. Each of the third band 54 and the fourth band 56 extends through the same first torso channel 42 and the same second torso channel 44.

A pair of shoulder pads 58 is provided and each of the shoulder pads 58 is integrated into the shirt 12 such that each of the shoulder pads 58 is aligned with a respective one of the user's shoulders when the shirt 12 is worn. Each of the shoulder pads 58 is aligned with respective ones of the channels 22 in the shirt 12. Additionally, each of the shoulder pads 58 is aligned with the first shoulder channel 36 and the second shoulder channel 40 of a respective one of the sets of shoulder channels 30. Each of the shoulder pads 58 is comprised of a resiliently compressible material thereby facilitating each of the shoulder pads 58 to enhance comfort for the user with respect to the plurality of elastomeric bands 48 compressing against the user. As is most clearly shown in FIG. 5, the shirt 12 includes a pair of pockets 60 that are each attached to an inside surface 62 of the shirt 12. Furthermore, each of the pockets 60 is aligned with the first shoulder channel 36 and the second shoulder channel 40 of a respective one of the sets of shoulder channels 30 and each of the pockets 60 has an open end 64. Each of the shoulder pads 58 is insertable into the open end 64 of a respective one of the pockets 60.

A waist belt 66 is movably integrated into the shirt 12 and each of the elastomeric bands 48 is attached to the waist belt 66. The waist belt 66 is tightenable for increasing tension in the elastomeric bands 48 to increase the support of the user's rotator cuffs. The waist belt 66 is loosenable for decreasing tension in the elastomeric bands 48 to decrease the support of the user's rotator cuffs. The waist belt 66 comprises a pair of side sections 68, a front section 70 and a back section 72. The front section 70 extends laterally across the front side 46 of the body portion 14 of the shirt 12, the back section 72 extends laterally across the back side 47 of the body portion 14 of the shirt 12, and each of the front section 70 and the back section 72 has a first end 74 and a second end 76.

The waist belt 66 includes a pair of first buckles 78 and each of the first buckles 78 is attached to a respective one of the first end 26 and the second end 28 of the front section 70. The waist belt 66 includes a pair of second buckles 80 and each of the second buckles 80 is attached to a respective one of the first end 26 and the second end 28 of the back section 72. Each of the first buckles 78 and the second buckles 80 adjustably engage a respective one of the side sections 68 of the waist belt 66 such that a diameter of the waist belt 66 is adjustable. Each of the first buckles 78 and the second buckles 80 comprises a first portion 82 that releasably engages a second portion 84 thereby facilitating the front section 70 and the back section 72 to be disconnected from the pair of side sections 68.

Each of the first buckles 78 and the second buckles 80 has a pair of slots 86 extending through respective first buckles 78 and respective second buckles 80. The pair of slots 86 has a primary portion 88 that is perpendicularly oriented with a secondary portion 90. Each of the elastomeric bands 48 extends inwardly into the primary portion 88 of a respective one of the slots 86 in a respective one of the first buckles 78 and second buckles 80. Additionally, each of the elastomeric bands 48 extends outwardly through the secondary portion 90 of the respective slot on the respective first buckle 78 and second buckle 80.

In use, the shirt 12 is worn by the user when the user is recovering from a shoulder injury. Each of the side sections 68 is either tightened or loosened to either increase or decrease the tension of the elastomeric bands 48. In this way the user's shoulders are supported while the shirt 12 is worn to facilitate the user's shoulders to heal from the injury. Additionally, the elastomeric bands 48 facilitate resistance to movement thereby facilitating the user's shoulders to be exercised while the shirt 12 is being worn. In this way the elastomeric bands 48 enhance the rehabilitation process of the user's shoulders after an injury or after having reconstructive surgery.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A joint rehabilitating garment assembly for supporting and rehabilitating an injured joint of a user, said assembly comprising:
   a shirt being wearable on a user's torso such that said shirt covers each of the user's shoulders, said shirt having a body portion, a pair of sleeves, a waist and a neck, said shirt having a plurality of channels being integrated into said shirt, each of said channels being positioned on said shirt such that each of said channels is positioned and configured to extend along pre-determined pressure points associated with supporting a rotator cuff injury in the user;
   a plurality of elastomeric bands, each of said elastomeric bands being routed through respective ones of said channels in said shirt thereby facilitating each of said elastomeric bands to extend along the pre-determined pressure points associated with rotator cuff injuries, each of said elastomeric bands imparting tension into the pre-determined pressure points wherein each of said elastomeric bands is configured to support the user's rotator cuffs while the user's rotator cuffs are healing from injury;
   a waist belt being movably integrated into said shirt, each of said elastomeric bands being attached to said waist belt, said waist belt being tightenable for increasing tension in said elastomeric bands wherein said waist belt is configured to increase the support of the user's rotator cuffs, said waist belt being loosenable for decreasing tension in said elastomeric bands wherein said waist belt is configured to decrease the support of the user's rotator cuffs;
   wherein said plurality of channels includes a pair of sets of shoulder channels;
   wherein each of said sets of shoulder channels extends over a respective shoulder of said shirt such that each of said shoulder channels extends over a respective one of the user's shoulders when said shirt is worn;
   wherein each of said sets of shoulder channels includes a first shoulder channel that is positioned between said neck and a crown of a respective one of said shoulders of said shirt wherein said first shoulder channel of each of said set of shoulder channels is configured to extend over a respective one of the user's supraspinatus tendon;
   wherein each of said sets of shoulder channels includes a second shoulder channel that is positioned on an opposing side of said crown of said respective shoulder of said shirt with respect to a respective one of said first shoulder channels wherein said second shoulder channel of each of said sets of shoulder channels is configured to extend over a respective one of the user's deltoid muscles over a lateral side of a shoulder joint of the user;
   wherein said plurality of channels includes a pair of sets of torso channels, each of said sets of torso channels being vertically oriented to extend along an axis extending between said neck and said waist of said shirt;
   wherein each of said sets of torso channels includes a first torso channel and a second torso channel;
   wherein said plurality of elastomeric bands includes a first band, a second band, a third band and a fourth band; and
   wherein said first band extends through said first torso channel of a respective one of said sets of torso channels and said second shoulder channel of a respective one of said sets of shoulder channels and said second torso channel of a respective one of said sets of torso channels.

2. The assembly according to claim 1, wherein each of said channels is integrated into an outer surface of said shirt, each of said channels having a first end and a second end, each of said first end and said second end of each of said channels being open, each of said channels being hollow.

3. The assembly according to claim 1, wherein:
   said first torso channel of each of said sets of torso channels is positioned on a front side of said body portion of said shirt, said first torso channel of each of said sets of torso channels being positioned on opposing sides of a center line of said body portion with respect to each other; and
   said second torso channel of each of said sets of torso channels is positioned on a back side of said body portion of said shirt with respect to each other, said second torso channel of each of said sets of torso channels being positioned on opposing sides of said center line of said body portion of said shirt.

4. The assembly according to claim 1, wherein said second band extends through said first torso channel of a respective one of said sets of torso channels and said first shoulder channel of a respective one of said sets of shoulder channels and said second torso channel of a respective one of said sets of torso channels.

5. The assembly according to claim 1, wherein said third band extends through said first torso channel of a respective one of said sets of torso channels and said second shoulder channel of a respective one of said sets of shoulder channels and said second torso channel of a respective one of said sets of torso channels.

6. The assembly according to claim 1, wherein said fourth band extends through said first torso channel of a respective one of said sets of torso channels and said first shoulder channel of a respective one of said sets of shoulder channels and said second torso channel of a respective one of said sets of torso channels.

7. The assembly according to claim 1, wherein:
each of said first band and said second band extends through a common first torso channel and a common second torso channel; and
each of said third band and said fourth band extends through a common first torso channel and a common second torso channel.

8. The assembly according to claim 1, further comprising a pair of shoulder pads, each of said shoulder pads being integrated into said shirt such that each of said shoulder pads is aligned with a respective one of the user's shoulders when said shirt is worn, each of said shoulder pads being aligned with respective ones of said channels in said shirt, each of said shoulder pads being aligned with said first shoulder channel and said second shoulder channel of a respective one of said sets of shoulder channels, each of said shoulder pads being comprised of a resiliently compressible material thereby facilitating each of said shoulder pads to enhance comfort for the user with respect to said plurality of elastomeric bands compressing against the user.

9. The assembly according to claim 1, wherein said waist belt comprises a pair of side sections, a front section and a back section, said front section extending laterally across said front side of said body portion of said shirt, said back section extending laterally across said back side of said body portion of said shirt, each of said side sections extending between said front section and said back section, each of said front section and said back section has a first end and a second end.

10. The assembly according to claim 9, wherein:
said waist belt includes a pair of first buckles, each of said first buckles being attached to a respective one of said first end and said second end of said front section;
said waist belt includes a pair of second buckles, each of said second buckles being attached to a respective one of said first end and said second end of said back section; and
each of said first buckles and said second buckles adjustably engages a respective one of said side sections of said waist belt such that a diameter of said waist belt is adjustable.

11. The assembly according to claim 10, wherein each of said first buckles and said second buckles has a pair of slots extending through respective first buckles and respective second buckles, said pair of slots having a primary portion being perpendicularly oriented with a secondary portion, each of said elastomeric bands extending inwardly into said primary portion of a respective one of said slots in a respective one of said first buckles and second buckles, each of said elastomeric bands extending outwardly through said secondary portion of said respective slot on said respective first buckle and second buckle.

12. A joint rehabilitating garment assembly for supporting and rehabilitating an injured joint of a user, said assembly comprising:
a shirt being wearable on a user's torso such that said shirt covers each of the user's shoulders, said shirt having a body portion, a pair of sleeves, a waist and a neck, said shirt having a plurality of channels being integrated into said shirt, each of said channels being positioned on said shirt such that each of said channels is positioned and configured to extend along pre-determined pressure points associated with supporting a rotator cuff injury in the user, each of said channels being integrated into an outer surface of said shirt, each of said channels having a first end and a second end, each of said first end and said second end of each of said channels being open, each of said channels being hollow, said plurality of channels including a pair of sets of shoulder channels and a pair of sets of torso channels, each of said sets of shoulder channels extending over a respective shoulder of said shirt such that each of said shoulder channels extends over a respective one of the user's shoulders when said shirt is worn, each of said sets of shoulder channels including a first shoulder channel that is positioned between said neck and a crown of a respective one of said shoulders of said shirt wherein said first shoulder channel of each of said set of shoulder channels is configured to extend over a respective one of the user's supraspinatus tendon, each of said sets of shoulder channels including a second shoulder channel that is positioned on an opposing side of said crown of said respective shoulder of said shirt with respect to a respective one of said first shoulder channels wherein said second shoulder channel of each of said sets of shoulder channels is configured to extend over a respective one of the user's deltoid muscles over a lateral side of a shoulder joint of the user, each of said sets of torso channels being vertically oriented to extend along an axis extending between said neck and said waist of said shirt, each of said sets of torso channels including a first torso channel and a second torso channel, said first torso channel of each of said sets of torso channels being positioned on a front side of said body portion of said shirt, said first torso channel of each of said sets of torso channels being positioned on opposing sides of a center line of said body portion with respect to each other, said second torso channel of each of said sets of torso channels being positioned on a back side of said body portion of said shirt with respect to each other, said second torso channel of each of said sets of torso channels being positioned on opposing sides of said center line of said body portion of said shirt;
a plurality of elastomeric bands, each of said elastomeric bands being routed through respective ones of said channels in said shirt thereby facilitating each of said elastomeric bands to extend along the pre-determined pressure points associated with rotator cuff injuries, each of said elastomeric bands imparting tension into the pre-determined pressure points wherein each of said elastomeric bands is configured to support the user's rotator cuffs while the user's rotator cuffs are healing from injury, said plurality of elastomeric bands including a first band, a second band, a third band and a fourth band, said first band extending through said first torso channel of a respective one of said sets of torso channels and said second shoulder channel of a respective one of said sets of shoulder channels and said second torso channel of a respective one of said sets of torso channels, said second band extending through said first torso channel of a respective one of said sets of torso channels and said first shoulder channel of a respective one of said sets of shoulder channels and said second torso channel of a respective one of said sets of torso channels, said third band extending through said first torso channel of a respective one of said sets of torso channels and said second shoulder channel of a respective one of said sets of shoulder channels and said second torso channel of a respective one of said sets of torso channels, said fourth band extending through said first torso channel of a respective one of said sets of torso channels and said first shoulder channel of a respective one of said sets of shoulder channels and said second torso channel of a respective one of said sets of torso channels, each of said first band and said second band extending through the same first torso channel and the same second torso channel, each of said third band and said fourth band extending through the same first torso channel and the same second torso channel;

a pair of shoulder pads, each of said shoulder pads being integrated into said shirt such that each of said shoulder pads is aligned with a respective one of the user's shoulders when said shirt is worn, each of said shoulder pads being aligned with respective ones of said channels in said shirt, each of said shoulder pads being aligned with said first shoulder channel and said second shoulder channel of a respective one of said sets of shoulder channels, each of said shoulder pads being comprised of a resiliently compressible material thereby facilitating each of said shoulder pads to enhance comfort for the user with respect to said plurality of elastomeric bands compressing against the user; and a waist belt being movably integrated into said shirt, each of said elastomeric bands being attached to said waist belt, said waist belt being tightenable for increasing tension in said elastomeric bands wherein said waist belt is configured to increase the support of the user's rotator cuffs, said waist belt being loosenable for decreasing tension in said elastomeric bands wherein said waist belt is configured to decrease the support of the user's rotator cuffs, said waist belt comprising a pair of side sections, a front section and a back section, said front section extending laterally across said front side of said body portion of said shirt, said back section extending laterally across said back side of said body portion of said shirt, each of said front section and said back section having a first end and a second end, said waist belt including a pair of first buckles, each of said first buckles being attached to a respective one of said first end and said second end of said front section, said waist belt including a pair of second buckles, each of said second buckles being attached to a respective one of said first end and said second end of said back section, each of said first buckles and said second buckles adjustably engaging a respective one of said side sections of said waist belt such that a diameter of said waist belt is adjustable, each of said first buckles and said second buckles having a pair of slots extending through respective first buckles and respective second buckles, said pair of slots having a primary portion being perpendicularly oriented with a secondary portion, each of said elastomeric bands extending inwardly into said primary portion of a respective one of said slots in a respective one of said first buckles and second buckles, each of said elastomeric bands extending outwardly through said secondary portion of said respective slot on said respective first buckle and second buckle.

\* \* \* \* \*